United States Patent [19]

Möller et al.

[11] Patent Number: 5,190,752
[45] Date of Patent: Mar. 2, 1993

[54] INTRAVENOUSLY ADMINISTERABLE POLYCLONAL IMMUNOGLOBULIN PREPARATION CONTAINING IGM AND METHOD OF MANUFACTURE

[75] Inventors: Wolfgang Möller, Oberursel; Hebert Dichtelmüller, Sulzbach/Ts.; Norbert Kothe, Kronberg; Dieter Rudnick, Rödermark; Detlef Piechaczek, Münster, all of Fed. Rep. of Germany

[73] Assignee: Biotest Pharma GmbH, Dreieich, Fed. Rep. of Germany

[21] Appl. No.: 380,180

[22] Filed: Jul. 14, 1989

[30] Foreign Application Priority Data

Jul. 27, 1988 [DE] Fed. Rep. of Germany ........ 3825429

[51] Int. Cl.$^5$ ..................... A61K 39/395; C07K 3/12; C07K 3/24; C07K 3/28
[52] U.S. Cl. .............................. 424/85.8; 530/387.1; 530/416; 530/417; 530/421
[58] Field of Search ......................... 424/85.8; 530/387

[56] References Cited

U.S. PATENT DOCUMENTS

| | | | |
|---|---|---|---|
| 4,165,370 | 8/1979 | Coval | 424/85.8 |
| 4,318,902 | 3/1982 | Stephan | 424/85.8 |
| 4,371,520 | 2/1983 | Uemura et al. | 530/387 |
| 4,482,483 | 11/1984 | Curry et al. | 424/85.8 |
| 4,540,573 | 9/1985 | Neurath et al. | 530/387 |
| 4,604,235 | 8/1986 | Flashner | 530/387 |
| 4,650,772 | 3/1987 | Dodge et al. | 530/387 |

FOREIGN PATENT DOCUMENTS

| | | |
|---|---|---|
| 0013901 | 8/1980 | European Pat. Off. . |
| 0038667 | 10/1981 | European Pat. Off. . |
| 0162462 | 11/1985 | European Pat. Off. . |
| 0303088 | 2/1989 | European Pat. Off. . |
| 0345543 | 12/1989 | European Pat. Off. . |
| 3604947 | 8/1987 | Fed. Rep. of Germany . |
| 3640513 | 6/1988 | Fed. Rep. of Germany . |

OTHER PUBLICATIONS

Steinbuch et al. (1973). Prep. Biochem. 3(4):363-373.
Saif et al. (1972). Inf. Immun. 6(4):600-609.
Prince et al. (1985). Cancer Res. 45:4592s-4594s.
Prince et al. (1985, J. Med. Virol. 16:119-125.
Barandun, Castel et al, "Clinical Tolerance and Catabolism . . . ", Vox Sang. 28 (1957), pp. 157-175.
Barandum, Kistler et al, "Intravenous Administration of Human . . . ", Vox Sang. 7 (1982), pp. 157-174.
Stephan and Dichtelmüller, "Comparison of in vitro Behaviour . . . ", Arzneimittel Forsch/Drug Res. 33 (II) (1983, 11, pp. 1538-1540).
"Complement and Complement Fixation", Mayer, Experimental Immunochemistry, 2nd ed. (1964), pp. 133-240 (Chapter 4).
E. Neter, "Bacterial Hemagglutination and Hemolysis", Bact. Rev. 20 (1956) pp. 166-187.
Bleeker/Agterberg/Rigter/deVries-van Rossen/Bakker, pp. 281-290, Vox Sang. 52, (1987).
*Immune Consequences of Trauma, Shock and Sepsis*, Springer-Verlag, Berlin, 1989, Eds. Faist et al.
"Investigations to Demonstrate the Antibacterial and Antitoxic Efficacy of an IgM-Enriched Intravenous Immunoglobulin Preparation", W. Stephen, pp. 501-507.
Friesen et al, "Column Ion Exchange Chromatographic Production of Human . . . ", Vox Sang., V. 48 (1985), pp. 201-212.
Van der Hoven et al, "The Isolation of Immunogenically Pure IgM from Cohn . . . ", Immunochemistry, vol. 10 (1973), pp. 107-114.

*Primary Examiner*—Robert A. Wax
*Assistant Examiner*—Richard C. Ekstrom
*Attorney, Agent, or Firm*—Sprung Horn Kramer & Woods

[57] ABSTRACT

An intravenously administrable polyclonal immunoglobulin preparation for the treatment and prophylaxis of bacterial infections containing at least 50% by weight of IgM in terms of the total content of immunoglobulin, exhibiting a low anticomplementary activity, being stable in aqueous solution, and being free of viruses. It can also consist of or also contain a mixture of several monoclonal IgM antibodies. The source material for its manufacture is an immunoglobulin-containing fraction of human, animal, or bacterial provenance. The fraction is treated with an anion exchanger that is eluted with a saline or pH gradient and the eluate is optionally subjected to gel filtration, treated before or after the chromatography with β-propiolactone and PEG 4000, and optionally heated. Treatment with β-propiolactone and ultraviolet light, treatment with solvents and detergents, or pasteurization can also be conducted. Proteins, sugars, or mixtures of amino acids are optionally added to the preparation.

13 Claims, No Drawings

INTRAVENOUSLY ADMINISTERABLE POLYCLONAL IMMUNOGLOBULIN PREPARATION CONTAINING IGM AND METHOD OF MANUFACTURE

Immunoglobulins play a very important part in combating infections in humans. Immunoglobulins are not uniform substances and can be assigned to various classes with various biochemical and physiological properties. It is especially IgG that participates in defending against viral agents, whereas the IgM antibodies combat preferably bacterial infections.

Due to its pentameric structure, IgM is especially appropriate for agglutinating bacteria. It also activates 100 to 400 times more complement than IgG and is 100 times more effective in opsonizing bacteria than monomeric IgG.

The administration of preparations that contain IgM should accordingly be especially effective for the treatment of bacterial infections. Immunoglobulin preparations have been successfully employed for 30 years in clinical practice for the treatment and prophylaxis of a wide range of diseases. These substances, however, have been predominantly pure IgG preparations, possibly with traces of IgA and IgM. Although the first preparations were tolerable only intramuscularly, intravenous IgG preparations have also been available for more than 20 years. Steps in the methods of decreasing anticomplementary activity and hence of ensuring intravenous compatibility are described in the literature (Schultz, H. E. and Schwick, G., Dtsch. med. Wochenschrift 87 (1962), 1643; Barandun, S. et al., Vox Sang. 28 (1957), 157; Barandun, S. et al., Vox Sang. 7 (1962), 187; Stephen, W., Z. Klin. Chem. Klin. Biochem. 7 (1969), 282).

All of these methods were restricted to IgG until 1980, when the first and until now only example of an intravenously tolerable IgM preparation (Pentaglobin®) was described in European Patent 13 901. This immunoglobulin preparation, which is treated with 0.05 to 0.15% of β-propiolactone to make it intravenously tolerable, contains, in addition to 10% of IgM, 80% of IgG and 10% of IgA.

Other immunoglobulin preparations, such as those described in Russian Patent 836 831 and German Patent 2 404 265, are enriched to 20 to 30% in IgM, but are not intravenously tolerable.

Nor are such immunologically pure IgM preparations as those described by Van der Hofen in Immunochemistry 10 (1973), 107-14, appropriate for intravenous administration due to their high anticomplementary activity, and they have accordingly not been available so far for treating bacterial infections.

The only route so far for administering preparations with more than 20% of IgM has been the intramuscular one. This method is not only very painful, but also cannot be employed to administer larger amounts of IgM, to increase the concentration of IgM in the blood significantly.

The object of the invention is to make available a high-purity IgM concentrate appropriate for intravenous administration in the treatment and prophylaxis of bacterial infections.

This object is attained with an immunoglobulin preparation that contains at least 50% by weight of IgM in terms of the overall immunoglobulin content, has a low anticomplementary activity, and is stable in aqueous solution and free of viruses. A preparation of this type can be manufactured from an IgM-containing fraction obtained from plasma or other sources of human, animal, or bacterial provenance by treatment with an ion exchanger, eluting the exchanger with a saline gradient or pH gradient, and gelfiltration, whereby treatment with β-propiolactone, precipitation with PEG 4000, and optionally heating are conducted before or after chromatography. These procedures can be followed by such in-themselves known measures as treatment with β-propiolactone and ultraviolet light or with solvents and detergents, which also fulfill the function of sterilization.

It is also possible to manufacture the preparation from a mixture of several monoclonal IgM antibodies or to add one or more such antibodies to a preparation manufactured by the method just described.

The concentration of IgM is preferably at least 50%. The injectable preparation is a solution that contains a concentration of 1 to 20 and preferably 3 to 5 g/100 ml of the preparation in accordance with the invention.

It has surprisingly been discovered that the anticomplementary activity of a preparation manufactured by the method in accordance with the invention and containing more than 50% of IgM is so low that the preparation is intravenously tolerable. This result could not have been expected even from the information in European Patent 13 901, which concerns only an approximately 10% IgM solution that is additionally stabilized with 90% of IgG and IgA.

The antibacterial activity of the preparation in accordance with the invention was compared in animal tests with that of the 10% IgM preparation described in European patent 13 901. It was surprisingly discovered that the activity of the preparation in accordance with the invention was higher than could have been expected from its content of IgM. It was completely unexpectedly discovered that the antibacterial activity of the IgM concentrate could be increased by decreasing the content of IgG and IgA. In other words, specific concentration of IgM are particularly effective when as little IgG and IgA as possible are present.

An effect of this type cannot be achieved with IgM preparations manufactured at the state of the art because either too little can be administered intramuscularly or the proportion of IgG and IgA is too high.

How a preparation in accordance with the invention can be manufactured will now be described.

A fraction that contains IgM, preferably the Cohn Fraction III obtained by Cohn's alcohol fractionation or the IgM fraction that occurs during the chromatographic isolation of IgG from blood, is precipitated with 1 to 5% and preferably 2.5% caprylic acid. The supernatant that contains the IgM is applied to an anion exchanger, with DEAE, QAE, or QMA groups for example, at a pH of 5.5 to 7.5. The IgM fraction bound is eluted with a saline gradient or pH gradient. Subsequent to concentration by means of ultrafiltration, the IgM eluate is treated with 0.05 to 0.5 ml of β-propiolactone per 100 ml of IgM solution. This reaction is preferably carried out at 20° C. to 37° C. and at a pH of 7.0 to 9.0, preferably 8.0, for 1 to 10 hours until the β-propiolactone is completely consumed. For further decrease of the anticomplementary activity, the IgM solution is treated with 1 to 3% PEG 4000 and preferably with 2.5% PEG 4000 at 0° C. to 10° C. and preferably 5° C. at a pH of 4.5 to 5, and the precipitate is centrifuged out.

If the initial anticomplementary activity is very high, the IgM solution can optionally also be heated to 40° C. to 60° C. and preferably 57° C. for 0.5 to 4 hours and preferably 1 hour.

Subsequent to this treatment the concentrate will be more than 50% pure IgM in terms of the overall immunoglobulin. For further purification the solution can be chromatographed over a gel-chromatography material with an exclusion limit of more than 500 000 D, e.g. Sephacryl S400HR (a cross-linked co-polymer of allyl dextran and N,N'-methylene bis acrylamide with a useful fractionation range for globular proteins with MW $2\times10^4$–$8\times10^6$) or S300HR (a cross-linked co-polymer of allyl dextran and N,N'-methylene bis acrylamide with a useful fractionation range for globular proteins with MW $1\times10^4$–$1.5\times10^6$) or Sepharose CL6B. The measures for decreasing the anticomplementary activity can also be carried out in a different sequence. The treatment with β-propiolactone can for example be carried out before the anion-exchange chromatography and the heating after the exclusion chromatography or the heating can be carried out prior to the treatment with β-propiolactone and the precipitation with PEG 4000.

The IgM fraction is collected, processed in a known way, and filtered sterile.

The method of manufacture in accordance with the invention will now be described in greater detail with references to the following examples.

EXAMPLE 1

1 kg of Cohn's Paste III was dissolved in 5 1 of 0.1M acetate buffer at a pH of 5 and treated with 2.5% caprylic acid at 25° C. The precipitate was centrifuged 4 hours later and the supernatant dialyzed against 0.025M of tromethamine at a pH of 6.5. The solution was then added to a 3 l column with QA-Trisacryl-LS (a copolymer of the primary monomer N-acryloyl-2-amino-2-hydroxymethyl1,3-propanediol and a trimethylaminomethyl derivate of the monomer) in the same buffer. The IgM was retained by the adsorbent and was eluted with 0.3M sodium chloride. The eluate was concentrated to a protein content of 40 g/l, heated at 57° C. for one hour, and treated overnight with 0.15% β-propiolactone at 25° C. and a pH of 8.0. The solution was then treated with 2.5 g of PEG 4000 per 100 ml at a pH of 4,5, stirred for 1 hour at 4° C., and centrifuged. The supernatant was then chromatographed in a 20 1 column with Sephacryl S400 HR. The second fraction, which contained the IgM, was ultrafiltered and filtered sterile. The IgM content was 85% with 5% of IgG and 9% of IgA. The total content of immunoglobulin was 99%.

EXAMPLE 2

A pool obtained from 50 1 of human plasma was thawed at 4° C. and the cryoprecipitate was separated. The PPSB factors were removed with DEAE Sephadex and the fibrinogen by precipitation with 9% ethanol at a pH of 5.3. The residual plasma was adjusted to an anionic strength of 22 mM of tromethamine/HCl at a pH of 7.5. Chromatography was carried out in a 10 1 column with DEAETrisacryl-LS (a co-polymer of the primary monomer, N-acryloyl-2-amino-2-hydroxymethyl-1,3-propanediol and a diethyl-aminoethylderivate of the monomer) equilibrated with the same buffer. The retained IgM was eluted with 0.3M of sodium chloride at a pH of 7.0. The eluate was precipitated with 25% ethanol at −3° C. and a pH of 7.5 and the precipitate dissolved in 0.1M of acetate buffer at a pH of 5 to a protein content of 50 g/l. The solution was treated with 2.5% caprylic acid at 25° C. and a pH of 5 and the precipitate separated. The supernatant was treated with 0.11% β-propiolactone for 5 hours at 25° C. and a pH of 7, precipitated for 1 hour at 4° C. with 2.5 g of PEG 4000 per 100 ml, and centrifuged. The supernatant was chromatographed in 3 runs in a 20 l column with Sephacryl S400. The second fraction was ultrafiltered and filtered sterile. This fraction contained the IgM at a purity of 93% with 2% of IgG and 5% of IgA. The overall immunoglobulin content was 100%.

EXAMPLE 3

1 kg of Cohn's Paste III was precipitated with caprylic acid as described in Example 1 and the supernatant dialyzed against 0.025M of tromethamine at a pH of 7.0.

The solution was then added to a 3 l column filled with QMA Accell (amorphous silica with an acrylamide co-polymer containing quaternary aminomethyl functional groups) equilibrated with the same buffer. The IgM was retained by the adsorbent and, once the column had been washed it was eluted with 0.05M of sodium acetate at a pH of 4.5. The eluate was treated with PEG 4000 and β-propiolactone as described in Example 1. The supernatant was rebuffered in a 2 l column of Sephadex G 25, ultrafiltered, and filtered sterile.

The IgM content was 73% with 20% of IgA and 7% of IgG. The total immunoglobulin content was 100%.

The treatment with β-propiolactone can be accompanied by a treatment with β-propiolactone and ultraviolet light or with detergents and solvents, preferably tri-n-butylphosphate and Tween 80 (a polyoxyethylene sorbitan monooleate), or by pasteurization. This treatment can, like the heating, also follow gel filtration.

Proteins—preferably human albumin, sugars—preferably maltose, or mixtures of amino acids can also be added to the preparation.

An IgM concentrate manufactured in accordance with the invention was compared with the starting material, commercially available Pentaglobin containing IgG, IgA, and IgM, and with an IgG fraction manufactured from the same starting material. The results follow.

1. Characterization of the reference preparations

The immunoglobulins IgG, IgA, and IgM were determined nephelometrically with antisera. The overall protein content was determined by the Biuret method. The data for the individual test preparations are summarized in Table 1.

TABLE 1

| No. | Preparation | Protein (g/l) | IgG (mg/100 ml) | IgA (mg/100 ml) | IgM (mg/100 ml) |
|---|---|---|---|---|---|
| 1 | Pentaglobin ® | 51.5 | 3720 | 920 | 750 |
| 2 | IgG fraction | 48.9 | 3770 | 890 | 70 |
| 3 | IgM concentrate | 8.1 | 40 | 70 | 750 |

2. Animal tests

The antibacterial activity of the IgM concentrate in accordance with the invention (Preparation 3) was compared with those of Pentaglobin (Preparation 1) and an IgG fraction (preparation 2) in mice infected with Pseudomonas as described by Stephan, W. and Dichtelmüller, H., Comparison of in vitro behavior and in vivo efficacy of two 7s immunoglobulin preparations for intravenous use, Arzneimittel Forsch./Drug Res. 33 (II) (1983), 11, 1538-40. Table 2 shows the survival rates.

TABLE 2

Results of mouse-protection tests

| No. | Preparation | Mice surviving 21 hours after infection (%) |
|---|---|---|
| 1 | Pentaglobin ® | 47.6 |
| 2 | IgG fraction | 33.3 |
| 3 | IgM concentrate (invention) | 66.7 |
| 4 | Untreated | 9.5 |

The IgM concentrate in accordance with the invention (Preparation 3) accordingly has a protective activity that is significantly more powerful than those of Preparations 1 and 2, even though its protein content is only 1/5 of theirs.

3. Determining the anticomplementary activity (ACA)

The anticomplementary activity was determined, as a criterion of intravenous tolerability, by the Kabat and Mayer method (Mayer, M. M., Complement and complement fixation, in Kabat, E. A. and Mayer, M. M., eds., Experimental Immunochemistry, 2nd ed., Springfield, Ill., 1964, Thomas Brooks, 133-240). Table 3 summarizes the results obtained with commercially available preparations as compared with those of the IgM concentrate in accordance with the invention. All solutions were adjusted to 5 g/100 ml.

TABLE 3

Anticomplementary activity of intravenous immunoglobulin preparations

| No. | Preparation | IgM (%) | ACA ($\mu$1C 1:30/mg protein) |
|---|---|---|---|
| 1 | Intraglobin ® | 0 | 10 |
| 2 | Pentaglobin ® | 10 | 25 |
| 3 | IgM concentrate (invention) | 75 | 25 |

The data for the IgM concentrate in accordance with the invention is comparable with the value of the commercially available IgM containing preparation Pentaglobin.

4. Tests of virus inactivation

The IgM concentrate in accordance with the invention was spiked with Type $\Phi \times 174$ bacteriophages and with Sendai viruses. Sterilization was carried out with $\beta$-propiolactone (Prince, A. M., Horowitz, B., Dichtelmüller, H., Stephan, W., and Gallo, R. C., Quantitative assays for evaluation of HTLV-III inactivation procedures; Tri(n-butyl)phosphate, sodium cholate, and $\beta$-propiolactone, Cancer Research 45 (1985), 4592s-4594s), $\beta$-propiolactone plus ultraviolet light (Prince, A. M., Stephan, W., Dichtelmüller, H., Brotman, B., and Huima, T., Inactivation of the Hutchinson strain of non-A/non-B hepatitis virus by combined use of $\beta$-propiolactone and ultraviolet irradiation, J. med. Virol. 16 (1985), 119-25), solvent plus detergent (Prince, A. M., Horowitz, B., Dichtelmüller, H., Stephan, W., and Gallo, R. C., Quantitative assays for evaluation of HTLV-III inactivation procedures; Tri(n-butyl)phosphate, sodium cholate, and $\beta$-propiolactone, Cancer Research 45 (1985), 4592s-4594s), or pasteurization (10 hours at 60° C.) (Heimburger, N., Wormsbächer, W., and Kumpe, G., Pasteurized isoagglutinin-free Factor-VIII preparation and method of manufacture [in German], European Patent Application 0 173 242 (1985). Table 4 shows the results.

TABLE 4

Virus inactivation in IgM concentrates

| Protein (g/100 ml) | Virus | Sterilization | Inactivation ($\log_{10} \downarrow$) |
|---|---|---|---|
| 4 | $\Phi \times 174$ | BPL | >7 |
| 4 | $\Phi \times 174$ | BPL + UV | 7 |
| 0.5 | Sendai | solvent + detergent | >4.5 |
| 5 | $\Phi \times 174$ | pasteurization | >8.0 |

The results indicate such an effective sterilization that transmission of a virus by an IgM concentrate sterilized by one of the methods listed in Table 4 can be ruled out.

5. Tests of shelf life

The IgM concentrate in accordance with the invention was heated in the form of a 1.6% solution (1.2 g/100 ml of IgM) to 57° C. for 4 hours. It was tested for antibodies to the bacteria *E. coli*, Klebsiella, and Streptococci by means of Neter's passive hemagglutination method (PHA) (Neter, E., Bact. Rev. 20 (1956), 166). Table 5 shows the activities before and after heating.

TABLE 5

Reciprocal antibacterial-antibody titers in IgM concentrates as compared to Pentaglobin ®

| Antibody to | IgM-concentrate before heating | Pentaglobin | IgM-concentrate after heating | Pentaglobin |
|---|---|---|---|---|
| *E. coli* | 640 | 160 | 320 | 160 |
| Klebsiella | 1280 | 640 | 640 | 320 |
| Streptococci | 320 | | 160 | |
| *Strep. virid.* | 320 | 160 | 160 | 40 |

The IgM concentrate in accordance with the invention is accordingly heat-stable with respect to its immunological activity considering the tolerance of the method of determination (±1 titer step). It behaves with respect to shelf life like the commercially available IgM-containing preparation Pentaglobin ®.

It will be understood that the specification and examples are illustrative but not limitative of the present invention and that other embodiments within the spirit and scope of the invention will suggest themselves to those skilled in the art.

What is claimed is:

1. The method which comprises intravenously administering to a patient in need of treatment and prophylaxis relative to bacterial infections an intravenously administrable polyclonal immunoglobulin solution for the treatment and prophylaxis of bacterial infections,
   a) comprising at least 50% by weight of IgM in terms of the total content of immunoglobulins,
   b) exhibiting an anticomplementary activity of at most about 25 $\mu$l complement (1:30)/mg protein,
   c) in aqueous solution, at 57° C. for 4 hours losing a maximum of about 2 titer steps,
   d) being free of viruses, and
   e) having a protein concentration of 1 to 20 g/100 ml.

2. The method according to claim 1, wherein the immunoglobulin preparation additionally contains at least one of a protein, sugar or mixture of amino acids.

3. The method according to claim 1, wherein the immunoglobulin preparation additionally contains at least one of human albumin, maltose or mixture of amino acids.

4. The method of manufacturing an immunoglobulin preparation according to claim 1, comprising adsorbing the immunoglobulin-containing fraction on an ion exchanger, eluting with a saline or pH gradient and subjecting the eluate to gel filtration, contacting the immunologbulin- containing material before or after the anion-exchange chromatography or the gel filtration with β-propiolactone and PEG 4000 of a concentration of about 1 to 3%, and optionally heating.

5. The method according to claim 4, wherein the anion exchanger is a co-polymer of the primary monomer, N-acryloyl-2-amino-2-hydroxy-methyl-1,3-propanediol and a diethylaminoethyl derivate of the monomer, a co-polymer of the primary monomer N-acryloyl-2-amino-2-hydroxy methyl-1,3-propanediol and a trimethylaminomethyl derivate of the monomer, or amorphous silica with an acrylamide co-polymer containing quaternary aminomethyl functional groups.

6. The method according to claim 4, wherein the gel for the gel filtration is a cross linked co-polymer of allyl dextran and N,N'-methylene bis acrylamide with useful fractionation range for globular proteins with MW $1 \times 10^4 - 1.5 \times 10^6$, or a cross-linked copolymer of allyl dextran and N,N'-methylene bis acrylamide with a useful fractionation range for globular proteins with MW $1 \times 10^4 - 8 \times 10^6$.

7. The method according to claim 4, wherein the preparation is treated before or after anion-exchange chromatography or gel filtration with β-propiolactone or with β-propiolactone and ultraviolet light and with about 1 to 3% PEG 4000 at about 0° C. to 10° C., and a pH of about 4.5 to 5.

8. The method according to claim 4, wherein heating is carried out for about 0.5 to 5 hours at about 40° C. to 60° C.

9. The method according to claim 4, wherein the preparation is treated with tri-n-butyl phosphate, a polyoxyethylene sorbitan monooleate or sodium cholate before or after gel filtration.

10. The method according to claim 4, wherein the preparation is treated with tri-n-butyl phosphate and a polyoxyethylene sorbitan monooleate before or after gel filtration.

11. The method according to claim 4, wherein the preparation is pasteurized before or after gel filtration.

12. The method according to claim 4, including the further step of adding to the preparation at least one of a protein, sugar or mixture of amino acids.

13. The method according to claim 4, including the further step of adding to the preparation at least one of human albumin, maltose or mixture of amino acids.

* * * * *